United States Patent [19]

Keller et al.

[11] Patent Number: 4,603,111
[45] Date of Patent: Jul. 29, 1986

[54] PREPARATION OF BIOCATALYSTS IN BEAD FORM

[75] Inventors: Reinhold Keller, Bad Soden am Taunus; Günter Siegemund, Hofheim am Taunus, both of Fed. Rep. of Germany

[73] Assignee: Hoechst Aktiengesellschaft, Frankfurt am Main, Fed. Rep. of Germany

[21] Appl. No.: 539,749

[22] Filed: Oct. 6, 1983

[30] Foreign Application Priority Data

Oct. 8, 1982 [DE] Fed. Rep. of Germany ....... 3237341

[51] Int. Cl.$^4$ .................. C12N 11/04; C12N 11/00; C12N 11/16; C12N 11/08
[52] U.S. Cl. .................................. 435/182; 435/174; 435/177; 435/180
[58] Field of Search ................ 435/180, 182, 177, 174

[56] References Cited

U.S. PATENT DOCUMENTS

| | | | |
|---|---|---|---|
| 3,252,948 | 5/1966 | Manecke | 435/180 |
| 3,843,443 | 10/1974 | Fishman | 435/180 |
| 4,070,348 | 1/1978 | Kräemer et al. | 435/180 |
| 4,190,713 | 2/1980 | Kräemer et al. | 435/180 |

FOREIGN PATENT DOCUMENTS 2805607 8/1979 Fed. Rep. of Germany .

*Primary Examiner*—David M. Naff
*Assistant Examiner*—L. Krawczewicz
*Attorney, Agent, or Firm*—Finnegan, Henderson, Farabow Garrett and Dunner

[57] ABSTRACT

Biocatalysts in bead form which contain microorganisms are particularly advantageously obtained by radical polymerization of acrylamide with methylene-bis-acrylamide in aqueous-organic phase suspension when the organic phase is a highly fluorinated carbon compound. The biocatalysts thus obtained have high stability and activity and are suitable for biotechnical processes.

15 Claims, No Drawings

PREPARATION OF BIOCATALYSTS IN BEAD FORM

Biocatalysts are becoming of increasing importance for the direct production of primary and secondary metabolites. Practical examples in which there is industrial interest are as follows: the production of fructose from glucose using glucose isomerase, the preparation of 6-aminopenicillanic acid from penicillin G using penicillin acylase, the preparation of L-aspartic acid from ammonium fumarate using *E. coli* and the preparation of malic acid from fumaric acid using cells of *Brevibacterium ammoniagenes*.

The term "biocatalyst" is understood in industrial microbiology as being a biological system of whole-celled microorganisms or of enzymes which are immobilized on a macroscopic support.

Recently, the use of immobilized microorganisms as biocatalysts has been preferred because of the costs of preparation and from the viewpoint of multi-enzyme reactions. The biocatalysts are essentially prepared by physical inclusion of the microorganisms in a polymer matrix. A very wide variety of materials is used for the preparation of matrices of this type, using many different procedures, wherein the application of polymers of unsaturated carboxylic acids with low molecular weight, such as acrylic acid and its derivatives, have been found particularly useful.

Copolymers in bead form have been disclosed as supports for biologically active substances in German Offenlegungsschrift No. 2,343,633 (U.S. Pat. No. 4,070,348). According to the process described there, a monomer which can undergo radical polymerization and which has a group which reacts with primary amino groups or hydroxyl groups on biologically active substances to form a covalent bond, for example acrylamide, is subjected to radical polymerization with a compound having at least 2 carbon double bonds which can undergo radical polymerization, such as methylene-bis-acrylamide or -methacrylamide, in a hydrophobic organic solvent. The aqueous solution of the biologically active component, preferably an enzyme, is added in a further step.

According to German Offenlegungsschrift No. 2,805,607, not only is this separate addition of the biologically active component, in this case microorganisms, avoided, but it is also stated that the products obtained have higher mechanical stability. To obtain them, the bead polymerization is carried out in the presence of the cells in an aqueous-organic suspension, methacrylamide and methylene-bis-acrylamide undergoing radical polymerization. The microorganisms are added shortly before the gelling point of the system is reached, and uniform distribution is brought about. In this process, the gelling point is advantageously determined by measuring, in a comparison batch some time beforehand, the time from the start of polymerization to the onset of gel formation under the conditions of the preparation of this polymerization batch. The suspending liquid which is preferably used is a diester of terephthalic acid with alkanols having 1 to 10 carbon atoms.

These processes which have been mentioned are rather elaborate. It has now been found that a large number of microorganisms can be incorporated, in a simple process, in a biocatalyst in bead form by radical polymerization of the amide of a low molecular weight unsaturated carboxylic acid with methylene-bis-acrylamide in aqueous-organic suspension when the amide is acrylamide and when the organic phase essentially comprises a highly fluorinated carbon compound.

In this context, "essentially" is intended to indicate that, in addition to the highly fluorinated carbon compound, other organic compounds which do not interfere with the reaction and, of course, also do not adversely affect the biocatalyst can be present. Thus, in the case of living organisms, substances toxic to cells are, of course, excluded. On the other hand, auxiliaries, such as polymerization initiators or surface-active substances are included. For this reason, in the following text, the term "highly fluorinated carbon compound(s)" is used for simplicity, but this is not intended to exclude other compatible substances.

According to the statements in German Offenlegungsschrift No. 2,805,607, it was not to be expected that utilizable biocatalysts in bead form would be obtained with acrylamide. In addition, it is surprising that it was possible significantly to simplify the polymerization process by using the highly fluorinated carbon compounds in the organic phase. On the other hand, according to the statements in German Offenlegungsschrift No. 2,343,633, it was not to be expected that a biocatalyst in bead form containing cells could be prepared by radical polymerization of acrylamide with methylene-bis-acrylamide when the polymerization is carried out in a medium which contains water and the organic phase of which contains a highly fluorinated carbon compound.

In the following text, preferred embodiments of the invention are illustrated in more detail:

The microorganisms are employed as a wet agglomerate of cells of viable or dead organisms, advantageously as a washed agglomerate of cells which has been isolated by centrifugation and taken up in physiological saline. The monomers acrylamide and methylene-bis-acrylamide are added to this, the mixture is suspended, with vigorous stirring, in the highly fluorinated carbon compound and polymerization is started.

The catalysts which are preferably used are persulfates, such as potassium persulfate or ammonium persulfate, combined with an initiator, such as $\beta$-dimethylaminopropionitrile or N,N,N',N'-tetramethylethylenediamine.

The polymerization temperature is advantageously not above room temperature, and is preferably 5°–20° C., in particular 10°–15° C.

The ratio of aqueous to organic phases can vary within relatively wide limits. A volume ratio of 1:3 to 1:15 is advantageous, and 1:6 to 1:10 is preferred.

It is possible to use all highly fluorinated fluorocarbon compounds which are liquid in the indicated temperature range as the organic phase. The criterion of suitability is merely that at least half of all the bonds in the molecule are carbon-fluoride bonds. It is obvious that mixtures of suitable compounds are also suitable, for example compounds of the same structural type which are fluorinated to different extents, and mixtures of compounds of different classes of structure are also suitable.

In contrast, the boiling points of the highly fluorinated carbon compounds are not crucial. Compounds which are inherently gaseous at the temperature of the process require the application of pressure and are thus less advantageous. In general, compounds with high boiling points are relatively viscous, for which reason products with boiling points from 40° to 300° C., in particular 90°–200° C., in each case under normal pressure, are preferred.

Preferred compounds are perfluorinated saturated and unsaturated, linear or cyclic hydrocarbons, such as perfluorononane, perfluoro-1-nonene, 1,2-bis-perfluoro-n-butyl)ethylene, 1,2-bis-(perfluoro-n-hexyl)-ethylene, 1,2-bis-perfluoro-n-octyl)-ethylene, perfluorodecahydronaphthalene, perfluoro-1-methyldecahydronaphthalene, perfluoro-1,3-dimethylcyclohexane, perfluoromethyladamantane or perfluorodimethyladamantane and highly fluorinated hydrocarbons containing other halogen atoms, such as 2,3-dichloroperfluoro-2-methylpentane, 1-bromoperfluorooctane or 1-chloroperfluorooctane, ethers, such as perfluoro-2-(n-propoxy)propyl 1,2,2,2-tetrafluoroethyl ether, lower perfluoropolyalkoxypropyl 1,2,2,2-tetrafluoroethyl ethers, perfluorobutyltetrahydrofuran, perfluoropropyltetrahydrofuran, perfluoro-1,4-bis-(isopropoxy)butane or perfluoro-1,8-bis-(isopropoxy)octane, as well as amines, such as perfluorotri-n-butylamine or perfluorotri-n-propylamine.

The use of an emulsifier can be advantageous for stabilizing the suspension, about 2 ml of a non-ionic emulsifier advantageously being added per liter of highly fluorinated carbon compound.

The polymerization generally takes only a few minutes. The resulting biocatalyst beads generally have a diameter of about 2–3 mm and thus can easily be separated out. They are advantageously isolated by filtration and washing with water or, preferably, with physiological saline.

The bead form of the biocatalyst allows a very good space-time yield and gives rise to high stability and activity. Thus, use in every one of a wide variety of reactor types is possible. The invention thus also relates to the use of the catalysts prepared according to the invention in biotechnical processes.

In the following examples, unless otherwise specified, stated percentages relate to weight.

EXAMPLE 1

30 g of wet *Lactobacillus bulgaricus* cells which had been isolated by centrifugation were taken up with 85.5 g of acrylamide and 4.5 g of N,N'-methylene-bis-acrylamide in 300 ml of physiological saline and added, with vigorous stirring, to a mixture of 1 liter of perfluorononane and 2 ml of a non-ionic surfactant which mixture had previously been freed of oxygen using nitrogen. The polymerization was started at 10° C. with 0.3 g of ammonium persulfate, dissolved in 2 ml of 0.9% saline, and 0.5 ml of N,N,N',N'-tetramethylethylenediamine. The reaction was complete after about 5 minutes. The resulting beads were filtered off and thoroughly washed with physiological saline.

In order to determine the biological activity of the biocatalyst, some of the beads were added to glucose solution and the amount of lactic acid formed was measured by titration. Comparison with the same amount of free cells showed that the biocatalyst had 65% of the original activity.

After storage in 0.9% saline at 5° C. for 70 days, this catalyst still had about 50% of the original activity. Free cells stored under the same conditions were unusable after only 14 days.

EXAMPLE 2

60 g of wet yeast cells which had been isolated by centrifugation were taken up in 500 ml of physiological saline together with 171 g of acrylamide and 9.0 g of N,N'-methylene-bis-acrylamide and added, with vigorous stirring, to a mixture of 2 liters of perfluoro-1-nonene and 2 ml of a non-ionic surfactant which mixture had been freed of oxygen by passing through nitrogen. The polymerization was started at 10° C. with 0.3 g of ammonium persulfate, dissolved in 2 ml of 0.9% saline, and 0.5 ml of N,N,N',N'-tetramethylethylenediamine. The reaction was complete after about 5 minutes. The resulting biocatalyst beads were filtered off and thoroughly washed with physiological saline.

In order to determine the biological activity, some of the beads were added to a suitable nutrient medium and the formation of ethanol was determined by gas chromatography. Comparison with free yeast cells showed that no activity was lost due to the immobilization.

EXAMPLE 3

50 g of *E. coli* cells (ATCC 11 105) which had been isolated by centrifugation were taken up in 300 ml of physiological saline together with 50 g of acrylamide and 2.5 g of N,N'-methylene-bis-acrylamide and added, with vigorous stirring, to a mixture of 1.5 liters of 2,3-dichloroperfluoro-2-methylpentane and 1 ml of a non-ionic surfactant which mixture had been freed of oxygen by passing through nitrogen. The polymerization was started at 10° C. with 0.3 g of ammonium persulfate, dissolved in 2 ml of 0.9% saline, and 0.5 ml of N,N,N',N'-tetramethylethylenediamine. The reaction was complete after 5 minutes. The resulting biocatalyst beads were filtered off and thoroughly washed with physiological saline.

In order to determine the biological activity, some of the beads were added to penicillin G solution, and the 6-aminopenicillanic acid liberated was measured at pH 7.6 by titration. Comparison with the same amount of free cells showed that the biocatalyst had 41% of the original activity.

EXAMPLE 4

30 g of a wet yeast agglomerate (*Saccharomyces cerevisiae*) which had been isolated by centrifugation were taken up in 250 ml of physiological saline together with 8.0 g of acrylamide and 10 g of N,N'-methylene-bis-acrylamide and added, with vigorous stirring, to a mixture of 1 liter of perfluorononane and 1 ml of a non-ionic surfactant which mixture had been freed of oxygen passing through nitrogen. Polymerization was started at 10° C. with 0.3 g of ammonium persulfate, dissolved in 2 ml of 0.9% saline, and 0.5 ml of N,N,N',N'-tetramethylethylenediamine. Reaction was complete after about 5 minutes. The resulting biocatalyst beads were filtered off and thoroughly washed with physiological saline.

In order to determine the biological activity, some of the beads were added to a suitable nutrient medium which contained adenosine 5'-monophosphate, and the formation of ATP was determined.

We claim:
1. A process for the preparation of a biocatalyst in bead form, comprising:
   mixing microbial cells, acrylamide and, methylene-bis-acrylamide in an aqueous phase with an organic phase consisting essentially of a highly fluorinated carbon compound to form a suspension, and
   thereafter polymerizing the acrylamide and the methylene-bis-acrylamide monomers in the suspen- sion to produce polymer beads containing microbial cells therein.

2. The process of claim 1 wherein the highly fluorinated carbon compound is one in which at least half of all the bonds in the molecule are carbon/fluorine bonds.

3. The process of claim 2 wherein the highly fluorinated carbon compound is perfluoro-1-nonene, 2,3-dichloroperfluoro-2-methylpentane, or perfluro-nonane.

4. The process as claimed in claim 1, wherein the polymerization is started with a persulfate.

5. The process as claimed in claim 1, wherein the polymerization temperature is not above room temperature.

6. The process as claimed in claim 1, wherein the polymerization temperature is 5° to 20° C.

7. The process as claimed in claim 1, wherein the polymerization temperature is 10° to 15° C.

8. The process as claimed in claim 1, wherein the ratio of the volume of the aqueous phase to the organic phase is 1:3 to 1:15.

9. The process as claimed in claim 1, wherein the ratio is 1:6 to 1:10.

10. The process as claimed in claim 1, wherein the highly fluorinated compound is a liquid having a boiling point under normal pressure of 40° to 300° C.

11. The process as claimed in claim 1, wherein the highly fluorinated compound is a liquid having a boiling point under normal pressure of 90° to 200° C.

12. The process as claimed in claim 1, wherein the highly fluorinated carbon compound is a liquid perhalogenated highly fluorinated hydrocarbon wherein the halogen is other than fluorine.

13. The process as claimed in claim 1, wherein the highly fluorinated carbon compound is a liquid perfluorinated hydrocarbon.

14. The process as claimed in claim 1, wherein a polymerization initiator is added.

15. The process as claimed in claim 1, wherein a surface-active compound is added.

* * * * *